US008100884B2

(12) United States Patent  
Schweikert et al.

(10) Patent No.: US 8,100,884 B2  
(45) Date of Patent: Jan. 24, 2012

(54) CATHETER TUNNELER ADAPTER (75) Inventors: Timothy Schweikert, Levittown, PA (US); Mark Fisher, Sellersville, PA (US); Angela Wentling, Sassamansville, PA (US); W. Shaun Wall, North Wales, PA (US); Kevin Sanford, Chalfont, PA (US); Rodger Lyle, Schwenksville, PA (US)

(73) Assignee: Medical Components, Inc., Harleysville, PA (US)

( * ) Notice: Subject to any disclaimer, the term of this patent is extended or adjusted under 35 U.S.C. 154(b) by 499 days.

(21) Appl. No.: 10/889,816

(22) Filed: Jul. 13, 2004

(65) Prior Publication Data  
US 2005/0027282 A1 Feb. 3, 2005

Related U.S. Application Data (60) Provisional application No. 60/487,926, filed on Jul. 17, 2003, provisional application No. 60/495,077, filed on Aug. 14, 2003.

(51) Int. Cl.  
*A61M 39/00* (2006.01)

(52) U.S. Cl. ......... 604/533; 604/534; 604/538; 606/108

(58) Field of Classification Search .......... 604/524–527, 604/533–536, 538, 539; 403/329, 326; 606/108, 606/167, 185  
See application file for complete search history.

(56) References Cited

U.S. PATENT DOCUMENTS

| 4,013,310 A | 3/1977 | Dye |
| 4,103,941 A | 8/1978 | Stoll |
| 4,323,065 A | 4/1982 | Kling |
| 4,326,516 A * | 4/1982 | Schultz et al. ............... 604/533 |
| 4,329,987 A * | 5/1982 | Rogers et al. ............... 604/533 |

(Continued)

FOREIGN PATENT DOCUMENTS

EP 0157224 A2 3/1985

(Continued)

OTHER PUBLICATIONS

International Search Report mailed Apr. 29, 2005.

(Continued)

*Primary Examiner* — Kevin C Sirmons  
*Assistant Examiner* — Laura C Schell  
(74) *Attorney, Agent, or Firm* — Glenn M. Massina; Fox Rothschild LLP (57) ABSTRACT

An adapter assembly (120) for connecting a catheter assembly (50,52) to a tunneler (110) having a generally tubular body (122) having a first end (124), a second end (126) and a longitudinal axis ( )128 extending therethrough between the first end and the second end. The first end (124) of the adapter is constructed to engage the proximal end (114) of a trocar (110). The second end (126) of the adapter is constructed to releasably engage at least one catheter lumen (50,52). A slider (140) is disposed about the adapter (120) and is longitudinally slidable along the adapter. When the slider (140) is slid towards the second end (126) of the adapter, the slider engages a plurality of legs (134a-134d) on the adapter and biases the plurality of legs toward each other and the longitudinal axis of the adapter. A method of subcutaneously tunneling a catheter using the adapter assembly is also described that comprises inserting a catheter into a patient, connecting the proximal end of a trocar to the adapter assembly, releasably restraining at least one lumen of the catheter in the adapter, and tunneling the assembly.

30 Claims, 8 Drawing Sheets

U.S. PATENT DOCUMENTS

| | | | |
|---|---|---|---|
| 4,369,781 A | | 1/1983 | Gilson et al. |
| 4,405,163 A | * | 9/1983 | Voges et al. .................... 285/305 |
| 4,748,808 A | | 6/1988 | Hill |
| 4,895,570 A | | 1/1990 | Larkin |
| 5,052,386 A | * | 10/1991 | Fischer, Jr. ............... 128/207.15 |
| 5,344,414 A | * | 9/1994 | Lopez et al. .................. 604/533 |
| 5,356,396 A | | 10/1994 | Wyatt et al. |
| 5,944,732 A | | 8/1999 | Schweikert et al. |
| 6,190,371 B1 | * | 2/2001 | Maginot et al. ............... 604/523 |
| 6,423,053 B1 | * | 7/2002 | Lee ............................... 604/533 |
| 6,749,574 B2 | * | 6/2004 | O'Keefe ........................ 600/561 |
| 7,128,734 B1 | * | 10/2006 | Wilson et al. ................. 604/535 |
| 2001/0032023 A1 | * | 10/2001 | Herweck et al. ........... 623/23.72 |
| 2004/0176739 A1 | | 9/2004 | Stephens et al. |
| 2004/0186445 A1 | * | 9/2004 | Raulerson et al. ............ 604/250 |

FOREIGN PATENT DOCUMENTS

| | | |
|---|---|---|
| EP | 0183396 A1 | 10/1985 |
| GB | 2072288 A | 9/1981 |
| WO | WO 94/23775 | 10/1994 |
| WO | WO 99/03527 A1 | 1/1999 |

OTHER PUBLICATIONS

Supplementary European Search Report, EP 04 77 8089, dated May 7, 2007 (4 pages).

Communication Pursuant to Article 94(3) EPC, dated May 16, 2008; EP Application No. 04778089.5 (6 pages).

Office Action dated Nov. 4, 2009 of Japanese Appln. Serial No. 2006-520269 (2 pages)—translation only.

Examination Report dated May 28, 2010 of European Patent Application EP 04778089.5 (3 pages).

* cited by examiner

CATHETER TUNNELER ADAPTER

CROSS REFERENCE TO RELATED APPLICATION

This application claims the benefit of U.S. Provisional Application No. 60/487,926, filed Jul. 17, 2003 and U.S. Provisional Application No. 60/495,077, filed Aug. 14, 2003.

FIELD OF THE INVENTION

The present invention relates to a tunneler device for subcutaneously tunneling at least one catheter lumen under a patient's skin.

BACKGROUND OF THE INVENTION

Catheters for the introduction or removal of fluids may be located in various venous locations and cavities throughout the body of a patient for introduction of fluids to the body or removal of fluids from the body. Such catheterization may be performed by using a single catheter having multiple lumens. A typical example of a multiple lumen catheter is a dual lumen catheter in which one lumen introduces fluid and the other lumen removes fluid. An example of such a multiple lumen catheter is the SPLIT STREAM® catheter, sold by Medical Components, Inc. of Harleysville, Pa.

Generally, to insert any catheter into a blood vessel, the vessel is identified by aspiration with a long hollow needle in accordance with the well-known Seldinger technique. When blood enters a syringe attached to the needle, indicating that the vessel has been found, a thin guide wire is then introduced, typically through a syringe needle or other introducer device into the interior of the vessel. The introducer device is then removed, leaving the end portion of the guide wire that has been inserted into the vessel within the vessel and the opposing end of the guide wire projecting beyond the surface of the skin of the patient. At this point, several options are available to a physician for catheter placement. The simplest is to pass a catheter into the vessel directly over the guide wire. The guide wire is then removed, leaving the catheter in position within the vessel. However, this technique is only possible in cases where the catheter is of a relatively small diameter, made of a stiff material, and not significantly larger than the guide wire. For example, this technique may be used to insert small diameter dual lumen catheters into a patient. If the catheter to be inserted is significantly larger than the guide wire, a dilator and sheath assembly is passed over the guide wire to enlarge the hole. The guide wire and dilator are then removed, and the catheter is then inserted through the sheath and into the vessel. The sheath is then removed by peeling the sheath from around the catheter while pulling the sheath from the vessel.

For chronic catheterization, in which the catheter is intended to remain inside the patient for an extended period of time, such as for weeks or even months, it is typically desired to subcutaneously tunnel the catheter using various tunneling techniques. The catheter is typically tunneled into the patient prior to inserting the catheter into the patient's vein.

However, depending on the patient or the implanting surgeon's skill, there may be times when it is more advantageous to perform the tunneling after the catheter is implanted in the patient. For some catheters, though, such as multiple lumen catheters with a hub and catheters with bonded luers on the proximal ends of the catheters, it is impractical to perform the tunneling after the catheter is installed in the patient. It would be beneficial to provide a tunneling tool that provides a surgeon with alternative installation procedures for subcutaneously tunneling the catheter, either before or after the distal portion of the catheter is placed in the patient's blood vessel, that better suit either the patient's needs or the surgeon's skills.

In order to be able to perform the tunneling after the distal end of the catheter assembly is inserted into the patient, the proximal ends of each catheter must be attached to a tunneler device adapted to pull the proximal end of each catheter through the tunnel. After tunneling, the proximal ends of the catheters must be disconnected from the tunneler device connected to a catheter hub. It would be beneficial to provide a tunneler device that allows for the simultaneous tunneling of the proximal ends of each catheter in a multi-lumen catheter assembly. Likewise, it would be beneficial to provide a tunneler device that would allow for the simultaneous tunneling of the distal ends of each catheter in a multi-lumen catheter assembly.

SUMMARY OF THE INVENTION

The present invention provides a catheter tunneler adapter assembly. The assembly comprises an adapter that is adapted to be connected to a trocar and releasably connected to a catheter. The assembly is used for subcutaneously tunneling a catheter through a patient's flesh during the insertion of a long term hemodialysis catheter. The adapter has a distal end, a proximal end and a tubular body extending therethrough between the distal and proximal ends. The tubular body defines a longitudinal passageway along the longitudinal axis of the adapter. The distal end of the adapter is adapted to connect to the trocar. The connection of the adapter to the trocar can be either releasable or fixed. The proximal end of the adapter is adapted to releasably connect to a catheter. Generally the proximal end of the adapter has a plurality of tapered legs extending proximally from tubular body of the adapter. The legs preferably have stops located at the most proximal end of the adapter and there are preferably a plurality of ribs extending from the legs inward towards the longitudinal axis of the adapter. There is, disposed around the adapter, a slider that is sized to frictionally fit around the adapter and slide back and forth longitudinally along the adapter; the slider ensheathes the adapter and is free of radially outward projections, thereby presenting a minimal transverse dimension and generally smooth continuous outer surface that facilitates its being pulled through the subcutaneous tunnel with the catheter and adapter. The range of motion of the slider is limited by the stops at the proximal end and at least one bump located on the outside of the adapter's tubular body. Preferably, at least one of the plurality of legs is tapered in such a way that the legs are thicker at the proximal end of the adapter. The adapter is operated by inserting at least one catheter lumen into the proximal end of the adapter and sliding the slider proximally so that the slider compresses the tapered legs towards the longitudinal axis and each other, thereby restraining the catheter within the longitudinal passageway. Either the proximal end or the distal end of the catheter may be inserted into the adapter. Once the catheter is restrained within the adapter, the assembly is tunneled, trocar first, according to techniques well known to those skilled in the art.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings.

DETAILED DESCRIPTION OF THE INVENTION

In the drawings, like numerals indicate like elements throughout. Certain terminology is used herein for convenience only and is not to be taken as a limitation on the present invention. When describing or referring to the catheter tunneler adapter, the words "proximal" and "distal" refer to directions away from and closer to, respectively, the pointed tip of the trocar that makes up a portion of the catheter tunneling assembly according to the present invention. When describing or referring to a catheter, the words "proximal" and "distal" refer to directions away from and closer to, respectively, the tip of the catheter that is inserted in the blood vessel closest to the patient's heart. The terminology includes the words above specifically mentioned, derivatives thereof, and words of similar import. The following describes preferred embodiments of the invention. However, it should be understood based on this disclosure, that the invention is not limited by the preferred embodiments described herein.

Figure 1:
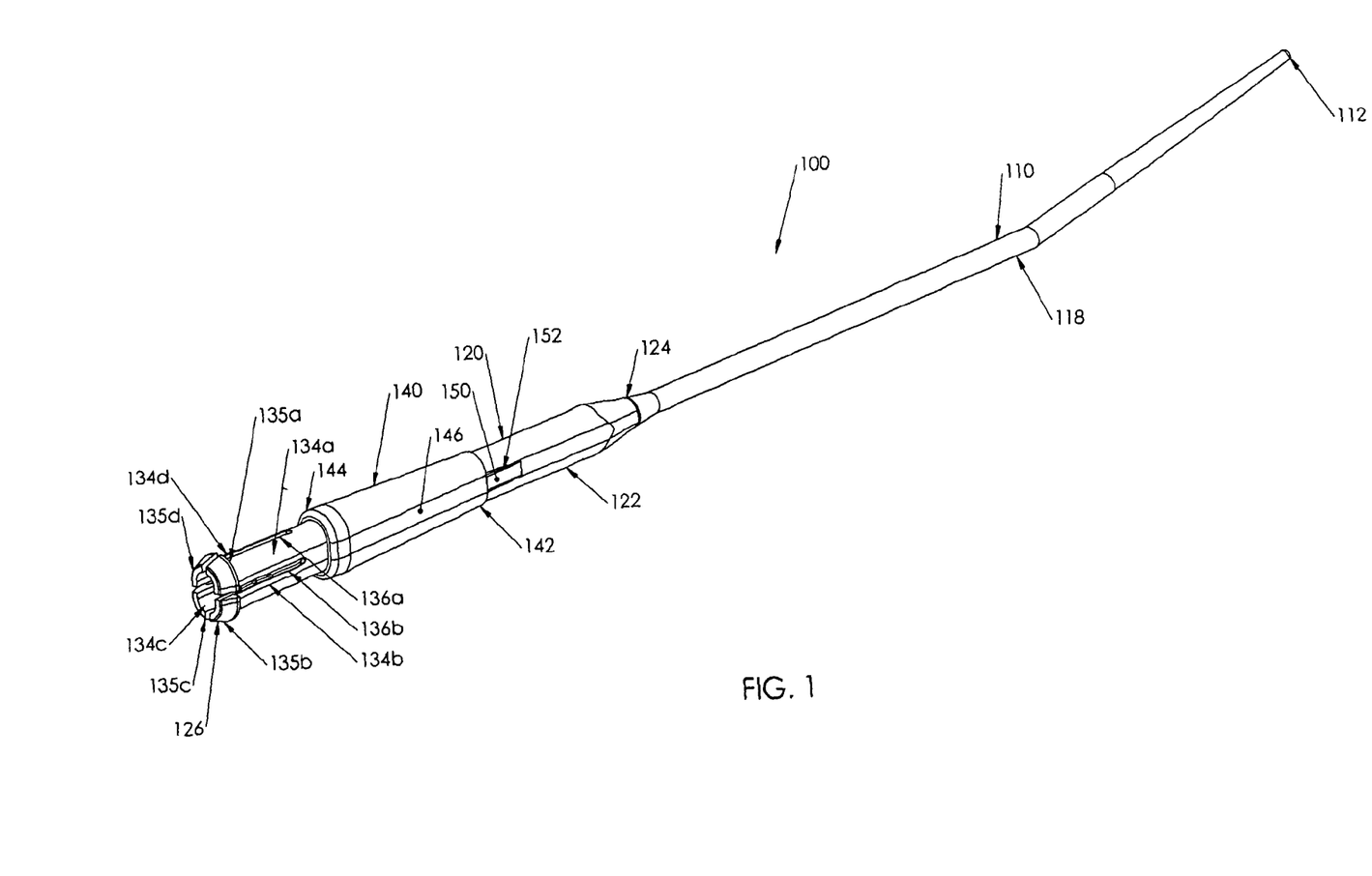
FIG. 1 is a perspective view of a catheter tunneler adapter, according to an embodiment of the present invention.

Referring to FIG. 1, a perspective view of a catheter tunneling assembly 100 according to a preferred embodiment of the present invention is shown. Preferably, the catheter tunneling assembly 100 is used to tunnel a distal end of a catheter assembly through a subcutaneous tunnel prior to inserting the catheter into the patient. Alternatively, the catheter tunneling assembly 100 may be used to tunnel a proximal end of the catheter assembly through the subcutaneous tunnel either prior to or after inserting the catheter into the patient.

Figure 2:
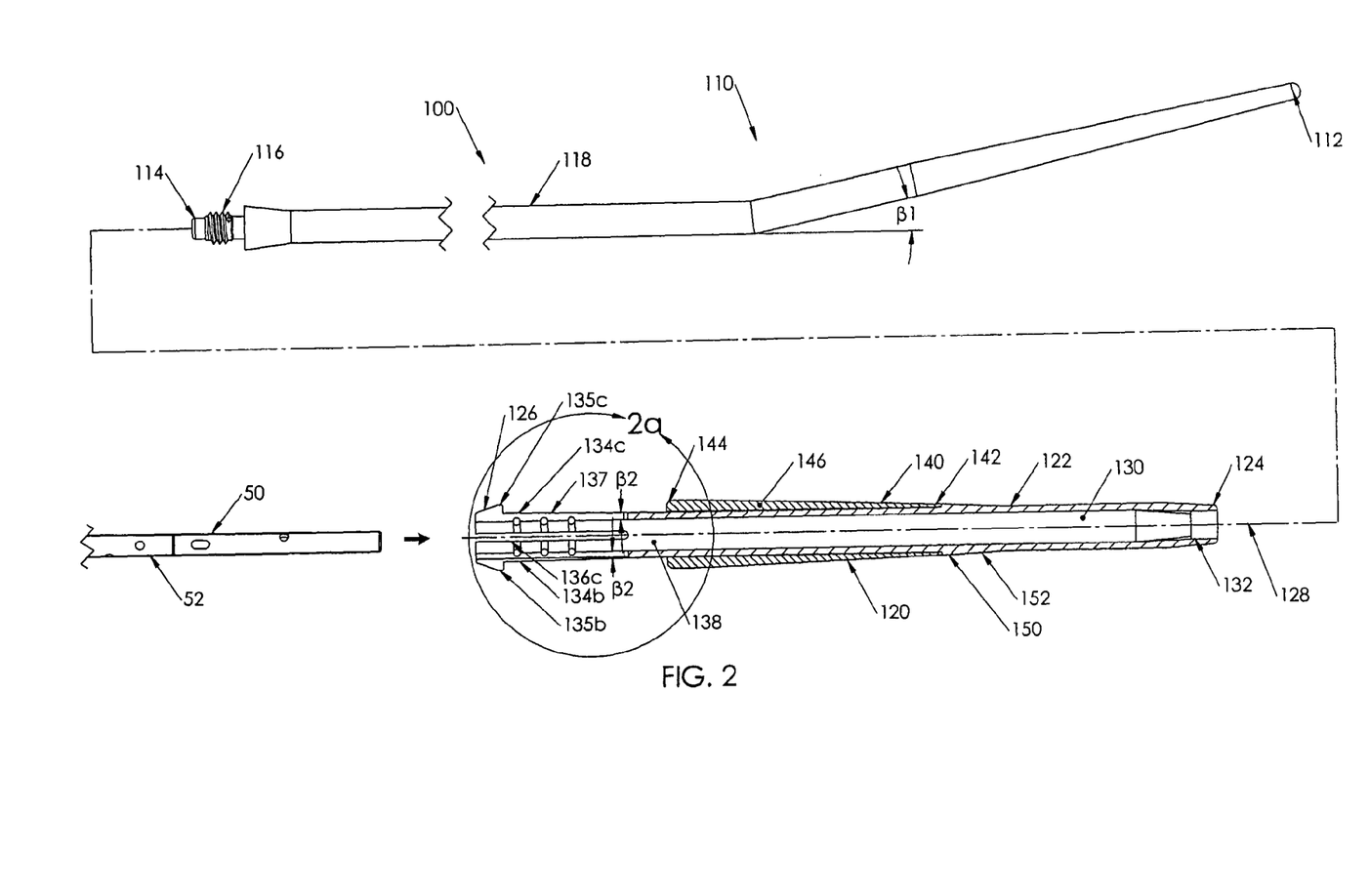
FIG. 2 is an exploded side view, partially in section, of the catheter tunneler adapter in FIG. 1 and showing a catheter end to be inserted into the adapter.

Referring to FIG. 2, the tunneling assembly 100 includes a distal portion, or tunneler, such as a trocar 110, which is comprised of a distal tip 112 and a proximal end 114. Preferably, the proximal end 114 includes a threaded male connection 116. Alternatively, the proximal end 114 of the trocar 110 may include a female threaded connection (not shown), bulbous or barbed projections (not shown) or a notch (not shown), a ridge (not shown), or any other type of suitable connection device in place of the threaded male connection 116.

The trocar 110 has an elongated body 118 that extends between the distal tip 112 and the proximal end 114. The body 118 preferably bends at a predetermined location along the length of the body 118. As shown in FIG. 2, the body 118 is bent at an angle $\beta 1$ of approximately 12 degrees, although those skilled in the art will recognize that the body 118 may be bent more or less than 12 degrees or have no bend at all.

Referring generally to FIGS. 1-4, the tunneling assembly 100 further includes a proximal portion, or adapter 120. The adapter 120 is comprised of a generally elongated tubular body 122 having a generally circular distal end 124, which tapers to a generally oblong proximal end 126. A longitudinal axis 128 extends between the distal end 124 and the proximal end 126.

Referring to FIG. 2, the distal end 124 of the adapter 120 includes a connection means or section for connecting the proximal end 114 of the trocar 110 thereto. The connection means comprises a generally tubular distal passageway 130 extending generally longitudinally through the tubular body 122 from the distal end 124 toward the proximal end 126 of the adapter 120. The distal passageway 130 preferably includes a threaded female connection 132 to threadingly engage the threaded male connection 116 on the trocar 110. Alternatively, the distal end of the adapter 120 may have a recess (not shown) to accept a notch located on the proximal end 114 of the trocar 110, a male threaded connection to be mated to a female threaded connection on the proximal end 114 of the trocar 110 or any other suitable connection device adapted to connect the adapter to the trocar 110.

Figure 2A:
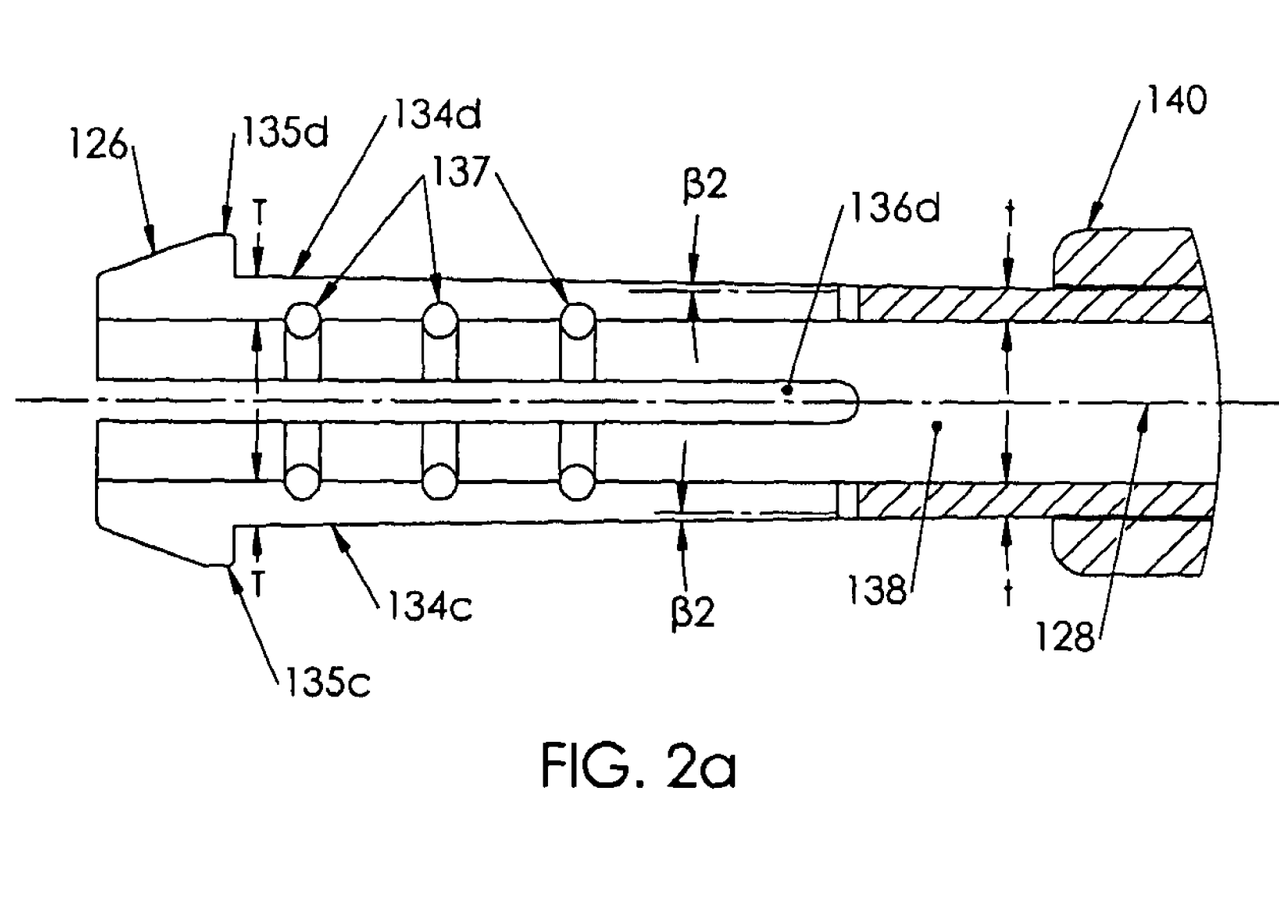
FIG. 2a is an enlarged side view, partially in section, of the catheter tunneler adapter in FIG. 2.
Figure 3:
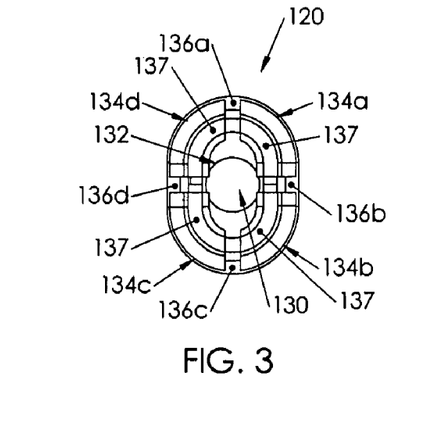
FIG. 3 is an end view of the adapter only of the catheter tunneler adapter in FIG. 1.

Referring to FIGS. 1-3, the proximal end 126 of the adapter 120 includes a connection means for connecting a plurality of catheter lumens 50, 52 thereto. The connection means comprises a plurality of legs 134a, 134b, 134c, 134d, which extend distally from the distal portion 124. A proximal portion of each leg 134a, 134b, 134c, 134d includes a stop portion 135a, 135b, 135c, 135d, respectively, that extends away from the longitudinal axis 128. A longitudinal slot 136a, 136b, 136c, 136d extends between each of adjacent legs 134d, 134a, 134b, 134c, 134d, respectively. While four legs 134a, 134b, 134c, 134d and four slots 136a, 136b, 136c, 136d are shown, those skilled in the art will recognize that more or less than four legs 134a, 134b, 134c, 134d and four slots 136a, 136b, 136c, 136d may be used.

As seen in FIG. 3, each leg 134a, 134b, 134c, 134d has a generally arcuate cross-section. A generally oval-shaped proximal passageway 138 is formed within a space defined by the legs 134a, 134b, 134c, 134d and the slots 136a, 136b, 136c, 136d. The proximal passageway 138 extends distally of the legs 134a, 134b, 134c, 134d toward the distal passageway 130.

Figure 4:
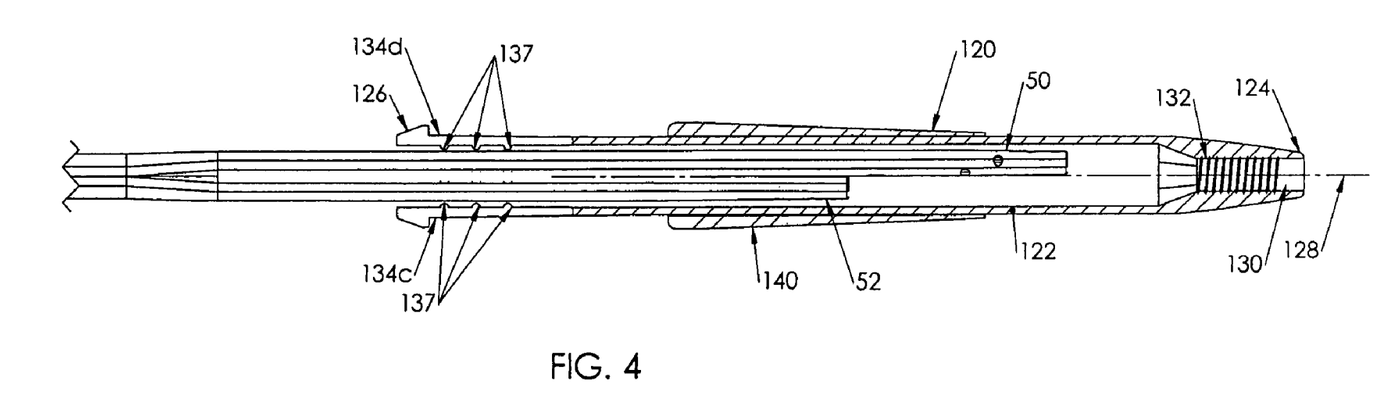
FIG. 4 is a side view, in section, of the adapter and slider of the catheter tunneler adapter in FIG. 1, with a multi-lumen catheter inserted therein.

Referring generally to FIGS. 2-4, optionally each leg 134a, 134b, 134c, 134d may include at least one, and preferably a plurality of lumen-engaging inner surface portions such as transverse ribs 137 that extend towards the longitudinal axis 128 into the proximal passageway 138. The transverse ribs 137 provide additional surface area to frictionally engage the lumens 50, 52 when the lumens 50, 52 are inserted into the distal end 126 of the adapter 120 and are engaged thereby, by pressing against the adjacent outer surface portions of the catheter lumens. The transverse ribs 137 may have a generally semi-circular cross-section, or the transverse ribs 137 may be barbed, to facilitate insertion of the lumens 50, 52 into the proximal passageway 138, but to retard removal of the lumens 50, 52 from the proximal passageway 138. Those skilled in the art will recognize that the ribs 137 may be of any shape that will facilitate the retention of the lumens 50, 52 within the proximal passageway 128 with sufficient frictional engagement as the catheter lumens are being pulled through the subcutaneous tunnel by the tunneler assembly.

As shown specifically in FIG. 2a, each leg 134c, 134d is tapered along an outer surface of each leg, distal from the longitudinal axis 128. Although not shown, legs 134a, 134b preferably have the same taper. Each taper has a thickness "t" proximate to the distal end 124 of the adapter 120. Each taper also has a thickness "T", thicker than the thickness "t", proximate to the proximal end 126 of the adapter 120. Preferably, the taper is at an angle β2, approximately 8 degrees, although those skilled in the art will recognize that the angle β2 may be more or less than 8 degrees. As also seen in FIG. 2, the proximal passageway 138 is in fluid communication with the distal passageway 130, although those skilled in the art will recognize that the proximal passageway 138 need not necessarily be in fluid communication with the distal passageway 130.

Figure 9:
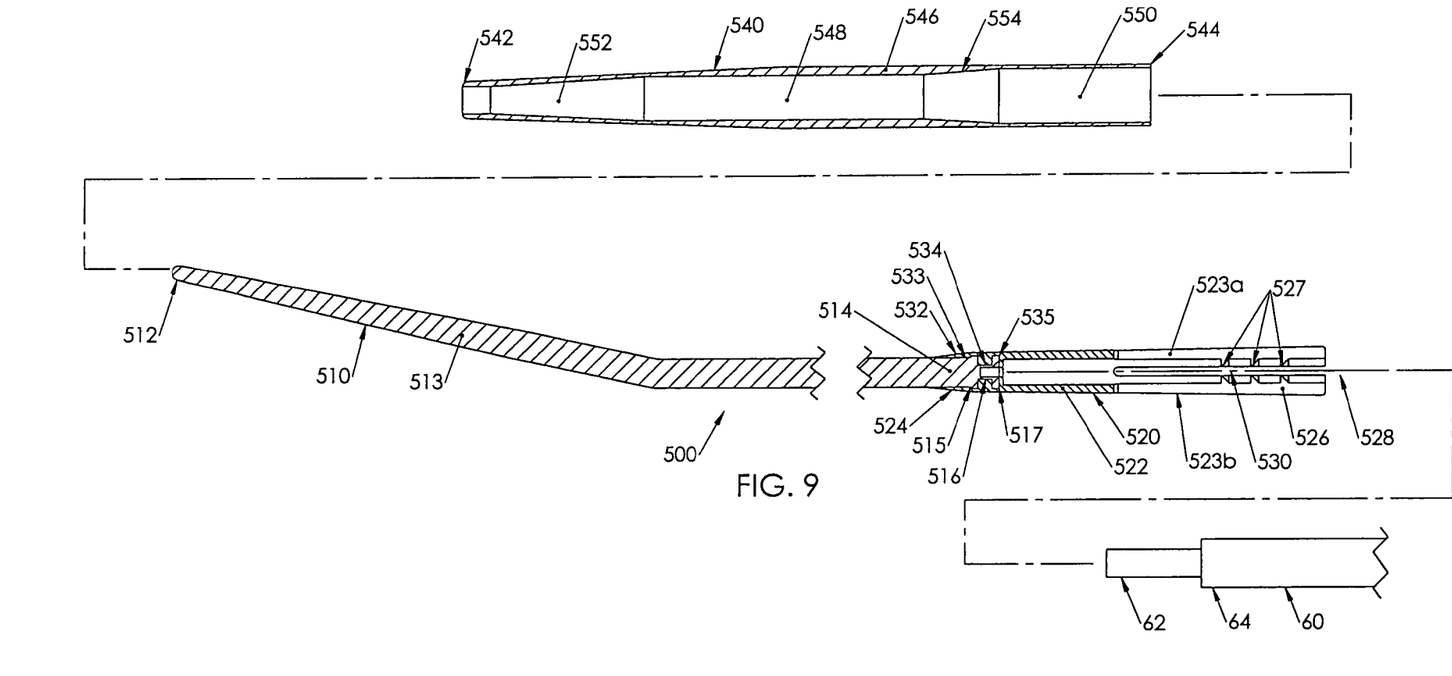
FIG. 9 is a side view, in section of an alternate embodiment of a catheter tunneler adapter, according to the present invention, with a slider being slid thereupon.

Referring to FIGS. 1, 2 and 2a, a locking member or slider 140 is slidably disposed on the adapter 120 distally from the legs 134a, 134b, 134c, 134d. The slider 140 is slidable between a distal position proximate to the distal end 124 of the adapter 120 and a proximal position proximate to the stops 135a, 135b, 135c, 135d. Preferably, the slider 140 is sized to frictionally engage and, due to the taper of the legs 134a, 134b, 134 c, 134d compress the legs 134a, 134b, 134c, 134d towards the longitudinal axis 128 and each other as the slider 140 is slid proximally about the adapter 120. Those skilled in the art will recognize that the slider 120 may have an elongated proximal portion designed to shield the distal end of the catheter lumens 50, 52 from obstructions during insertion. An example of such an elongated slider is shown in FIG. 9. Preferably, where a slider has an elongated proximal end, the slider covers any apertures that are disposed about the catheter lumens 50, 52.

As shown in FIGS. 1 and 2, the slider 140 has a distal end 142, a proximal end 144 and an elongated body 146 disposed between the distal end 142 and the proximal end 144. The slider 140 is sized to frictionally fit about the outside surface of the elongated tubular body 122 of the adapter 120. The slider also can be seen to be free of radially outward projections thereby having a minimal transverse dimension, and have a generally smooth, continuous outer surface thus being shaped and dimensioned to be suitable for facilitating its being pulled through the subcutaneous tunnel created by the trocar. The slider 140 is retained about the adapter 120 by at least one, and preferably two, raised tabs 150 located on opposing sides of the body 122 of the adapter 120. The raised tabs 150 are shaped and sized to allow the slider 140 to be slid over the raised tabs 150 in a proximal direction from the distal end 124 to the proximal end 126 to assemble the adapter 120, but restrict the movement of the slider 140 over the raised tabs 150 in the distal direction once the slider 140 is slid proximally past the raised tabs 150. As shown in FIG. 4, the raised tabs 150 preferably have a gradually sloped distal surface 152 and a vertical or steeply sloped proximal surface 154. Alternatively, the raised tabs 150 may be rounded or have any type of a profile that would facilitate sliding the slider 140 over the raised tabs 150 in the proximal direction and restrict the slider 140 from sliding over the raised tabs 150 in the distal direction. Preferably, the slider 140 and the adapter 120 are each of unitary construction and are constructed of a material that is sufficiently flexible as to allow the slider 140 to deflect enough to fit over the raised tabs 150 when a force is applied to the slider 140 in the proximal direction during assembly.

Preferably, in applications where the adapter 120 has an oval cross-section, the slider 140 has a generally oval cross-sectional shape to match the generally oval cross-sectional shape of the proximal passageway 138. However, those skilled in the art will recognize that the adapter 120 may have a cross-section that is circular or some other shape and that it is preferred that the slider 140 has a shape that corresponds to the cross-sectional shape of the adapter 120.

Referring generally now to FIGS. 1-4, during assembly of the adapter assembly 100, the slider 140 is positioned at the distal end 124 of the adapter 120. The slider 140 is then slid in a proximal direction around the adapter 120 until the entire slider 140 is proximal of the at least one raised tab 150, on the adapter 120.

Preferably, the adapter 120 and the slider 140 are constructed from a polymer, such as polypropylene or polyurethane, although those skilled in the art will recognize that the adapter 120 and the slider 140 may be of composite construction or may be constructed from other suitable materials as well. Examples of some other preferable materials would be TEFLON® polytetrafluoroethylene for the slider 140 and high density polypropylene for the adapter 120. Preferably, at least one of the slider 140 and adapter 120 are preferably constructed from a material that is rigid enough to minimize deflection and thereby restrain the slider 140 from inadvertently being slid over the raised tabs 150 in the distal direction. The trocar 110 is preferably of unitary construction and constructed from stainless steel. Those skilled in the art will recognize that the trocar 110 may be constructed from any material that is rigid enough to resist deflection during tunneling.

Figure 5:
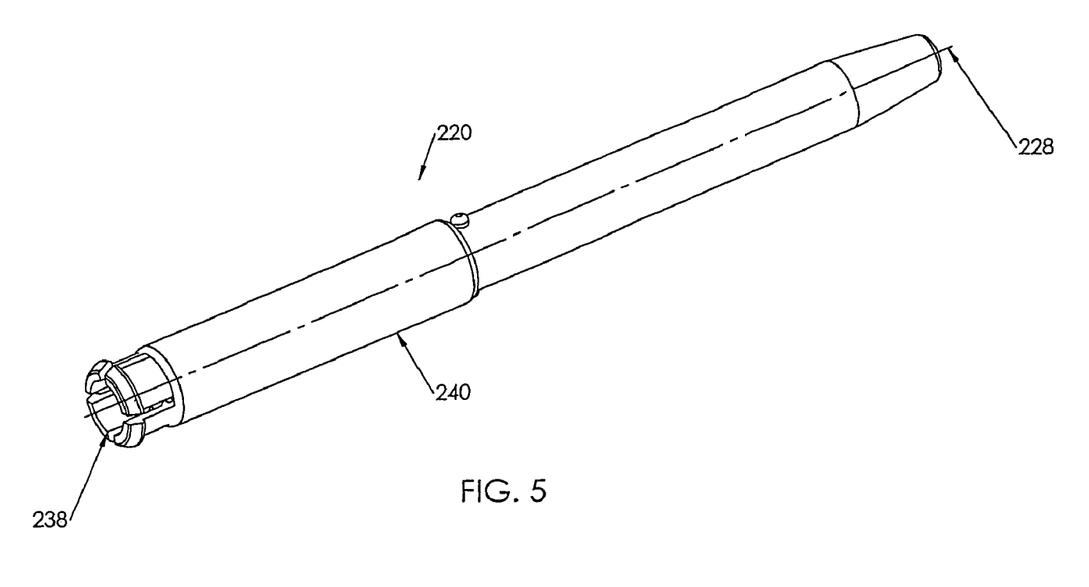
FIG. 5 is a perspective view of an alternate embodiment of a catheter tunneler adapter, according to the present invention.
Figure 6:
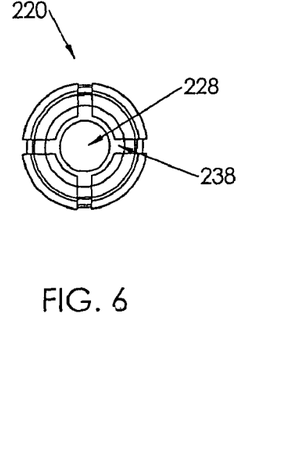
FIG. 6 is an end view of the adapter only of the catheter tunneler adapter in FIG. 5.

As seen in FIG. 2, a distal, or if preferred by the inserting physician a proximal, end of at least one, and preferably at least two, catheter lumens 50, 52 may be inserted into the proximal passageway 138. An example of such catheter lumens are the lumens used on the SPLIT STREAM® catheter, sold by Medical Components, Inc, of Harleysville, Pa. The lumens 50, 52 are insertable into the proximal passageway 138 at the proximal end 126 of the body 122. The lumens 50, 52 each have a generally circularly shaped cross-section, necessitating the need for the proximal passageway 138 in the adapter 120 to be generally oval shaped in cross-section. However, it will be known to those skilled in the art that in an application where the catheter to be tunneled has a generally circular cross-section, an adapter with a generally circular cross-section, such as the adapter 220 shown in FIGS. 5 and 6, is preferred. Referring back to FIG. 2, preferably, in a case where the inserting physician chooses to subcutaneously tunnel the catheter prior to insertion in the patient's vessel, if the lumen 50 is longer than the lumen 52, the distal passageway 138 is sufficiently long for both lumens 50, 52 to be at least partially inserted and retained therein.

Preferably, the slider 140 is disposed in the distal position prior to the lumens 50, 52 being inserted into the proximal passageway 138. The slider 140 may be disposed about the adapter 120 during manufacture, or the assembly 100 may be sold in pieces and the slider 140 may be disposed about the adapter 120 during post-sale assembly, prior to use. Preferably, the lumens 50, 52 are inserted into the proximal passageway 138 at least beyond the legs 134a, 134b, 134c, 134d, as shown in FIG. 4. The slider 140 is then slid proximally, toward the stops 135a, 135b, 135c, 135d. As the slider 140 is being slid along the length of the legs 134a, 134b, 134c, 134d, the taper in the legs 134a, 134b, 134c, 134d forces the legs 134a, 134b, 134c, 134d toward the longitudinal axis 128 and each other, thereby decreasing the size of the proximal passageway 138 proximate to the legs 134a, 134b, 134c, 134d, causing at least one of the legs 134a, 134b, 134c, 134d to frictionally engage at least one of the lumens 50, 52 and to force the lumens 50, 52 against each other, also in frictional engagement. The frictional engagement between the legs 134a, 134b, 134c, 134d and the catheter lumens 50, 52 is aided by the at least one transverse rib 137. The frictional engagement of the legs 134a, 134b, 134c, 134d with the lumens 50, 52 and of the lumens 50, 52 with each other restricts the lumens 50, 52 from being pulled out of the proximal passageway 138 during tunneling. The stops 135a, 135b, 135c, 135d prevent the slider 140 from being slid off the legs 134a, 134b, 134c, 134d. FIG. 4 shows the lumens 50, 52 after having been inserted into the proximal passageway 138 as described above. While FIG. 4 shows the catheter tunneler adapter assembly 100 that is not connected to the tunneler 110, it is preferable that the tunneler 110 is connected to the adapter 120 prior to insertion of the lumens 50, 52.

The trocar 110 is connected to the adapter 120 by inserting the proximal end 114 of the trocar 110 into the distal end 124 of the adapter 120. Those skilled in the art will recognize that the trocar 110 may be connected to the adapter 120 before or after releasably restraining the lumens 50, 52 in the adapter 120.

To tunnel the distal end of the catheter prior to insertion of the catheter into the patient, an incision is made in the patient's skin at the beginning of the tunnel. The distal tip 112 of the trocar 110 is inserted into the incision and the trocar 110 is advanced subcutaneously through fatty skin tissue to an exit point, such as at or near the incision site for the catheter to be inserted into the blood vessel being catheterized, thus defining a subcutaneous tunnel for anchoring the catheter assembly's proximal end, the tunnel being sized to be just large enough for the catheter. The trocar 110 is advanced through the tissue from the incision to the exit site, pulling the adapter 120 and the catheter lumens 50, 52 through the tunnel. As the trocar 110 exits the exit site, the trocar 110 may be gripped with a tool, such as forceps, and pulled from the exit site, until the entire tunneling assembly 100 is pulled from the exit site.

At this point, the slider 140 may be slid distally toward the distal end 124 of the adapter 120. Sliding the slider 140 distally allows the legs 134a, 134b, 134c, 134d to separate from each other as well as move away from the longitudinal axis 128, and into an unbiased position, thereby allowing the lumens 50,52 to be removed from the passageway 138. The lumens 50, 52 may then be removed from the adapter 120 and inserted into the incision site for insertion of the catheter into the vessel being catheterized.

Alternatively, the catheter may be retro-tunneled through a subcutaneous tunnel after the distal ends of the catheter lumens 50, 52 have been inserted into a patient's vessel. Preferably, the catheter has a detachable hub, such as the "SPLIT STREAM" catheter disclosed in U.S. Patent Publication No. US 2004/0092863, which is owned by the assignee of the present invention and is incorporated herein by reference in its entirety.

As described above, when retro-tunneling the catheter, the trocar 110 may be connected to the adapter 120 either before or after connecting the catheter lumens 50, 52 to the adapter 120. Also, the slider 140 is preferably disposed toward the distal end 124 of the adapter 120. However, those skilled in the art will recognize that the slider 140 may be initially disposed in the center of the adapter 120 or closer to the proximal end 126 of the adapter 120, where the slider 140 would have a smaller range of travel than that of a slider 140 disposed toward the distal end 124 of the adapter 120. With any type of fittings or extensions removed, proximal ends of the catheter lumens 50, 52 are inserted into the proximal passageway 138 in the adapter 120. The slider 140 is slid distally against the stops 135a, 135b, 135c, 135d to releasably retain the catheter lumens 50, 52 as described above and to ensheathe the adapter. The distal tip 112 of the trocar 110 is then inserted into the incision site where the catheter is inserted into the vessel being catheterized, and advanced through subcutaneous fatty tissue, either to a separate cut incision site, or by advancing the trocar 110 through the skin. Preferably, a trocar 110 that is used to pierce the skin of a patient will have a pointed tip 112 and a trocar 110 that is tunneled to a separate incision site would have a blunt tip. As the trocar 110 exits the exit site, the trocar 110 may be gripped with a tool, such as forceps, and pulled from the exit site, until the entire tunneling assembly 100 is pulled from the exit site.

At this point, the slider 140 may be slid distally toward the distal end 124 of the adapter 120, and the proximal ends of the catheter lumens 50, 52 may be removed from the adapter 120 and connected to a hub or extensions as necessary. Those skilled in the art will recognize that the distal end of the catheter, with lumens 50, 52, may be inserted into the vessel being catheterized at a time either prior to or subsequent to the above-described tunneling procedure.

While the tunneling assembly 100 is described herein as two separate parts, namely a trocar 110 and an adapter 120, those skilled in the art will recognize that the tunneling assembly 100 may be a single part, still with a slidable slider 140.

An alternate embodiment of an adapter 220 is shown in FIGS. 5 and 6. Instead of the generally oval shaped proximal passageway 138 shown in FIG. 3, the adapter 220 of FIGS. 5 and 6 includes a longitudinal axis 228 and a proximal passageway 238 having a generally circularly shaped cross-section, when a cross-sectional view is taken in a plane that is perpendicular to the longitudinal axis 228. Preferably, the slider 240 that accompanies the adapter 220, also has a generally circular cross-section. The generally circularly shaped cross-section of the proximal passageway 238 is shaped to accept and releasably retain two semi-circularly shaped lumens such as those on the SPLIT-CATH® catheter sold by Medical Components, Inc. Alternatively, the adapter 220 may be used to releasably retain a single circularly shaped lumen, such as the lumen used on the TESIO® catheter, also sold by Medical Components, Inc. The adapter 220 preferably connects to the trocar 110 in the manner described above with respect to the adapter 120, and a catheter may be subcutaneously tunneled in any of the manners described above with respect to the adapter 120.

Figure 7:
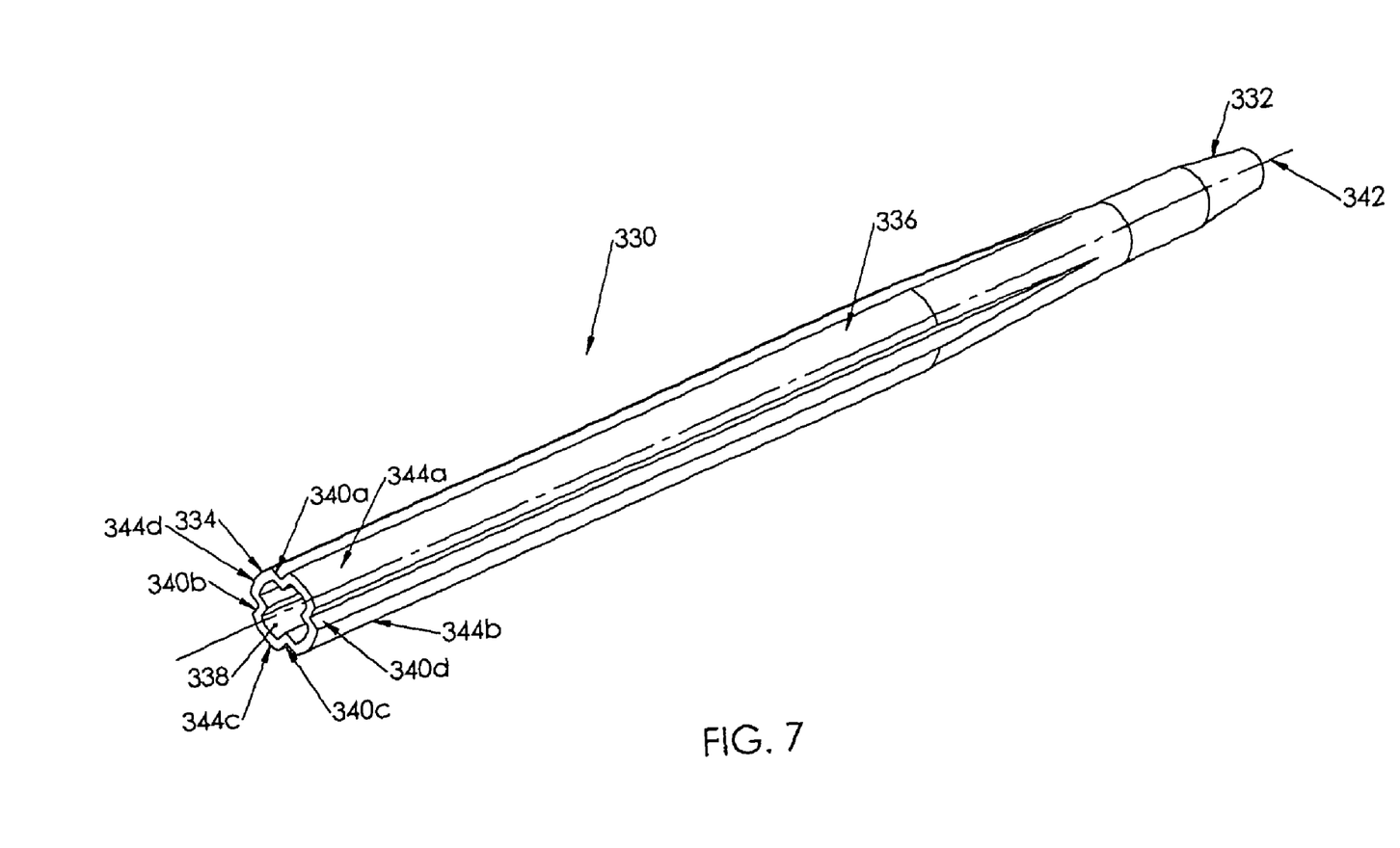
FIG. 7 is a perspective view of an alternate embodiment of an adapter only of a catheter tunneler adapter, according to the present invention.

A third embodiment of an adapter 330 is shown in FIG. 7. The adapter 330 has a distal end 332, a proximal end 334 and a longitudinal axis 342 extending therethrough between the distal end 332 and the proximal end 334. There is a longitudinal passageway 338 extending along the longitudinal axis 342 between the distal end 332 and the proximal end 334. The body of the adapter 330 comprises a plurality of legs 344a, 344b, 344c and 344d extending longitudinally, parallel to the longitudinal axis 342, along the adapter. Preferably, the adapter 330 is of unitary construction and has a plurality of flexible grooves 340a, 340b, 340c, 340d extending longitudinally from the distal end 332 to the proximal end 334 and located between the plurality of legs 344d, 344a, 344b, 344c and 344d. While the grooves 340a, 340b, 340c, 340d are shown in FIG. 7 to be V-shaped, those skilled in the art will recognize that grooves having a shape other than a V-shape, such as a U-shape, may also be used. Preferably, the adapter 330 has a generally round cross-section, although those skilled in the art will recognize that alternative embodiments may have cross-sections that are not round, such as an oval cross-section. The outside diameter of the distal end 332 is smaller than the outside diameter of the proximal end 334. There is, located between the distal end 332 and the proximal end 334, a tapered section 336, where the outside diameter of the adapter 330 increases from the distal end 332 towards the proximal end 334.

During use, a slider (not shown) may be slid proximally from the distal end 332 towards the proximal end 334. As the slider is slid proximally towards the distal end 332, the slider frictionally engages the exterior surface of the adapter 330, thereby compressing the proximal end 338 of adapter 330 towards the longitudinal axis 328 and decreasing the diameter of the longitudinal passageway 338. Preferably, the inner diameter of the slider is sized to compress the adapter 330 by frictionally engaging the tapered portion 336 of the adapter 330 as the slider is slid proximally along the longitudinal axis 342. Preferably, the longitudinal passageway 338 has a cross-sectional area sized so that a part of a catheter may be inserted into the proximal end 334 of the adapter 330 when the slider is in the distal position and, when the slider is slid proximally to the proximal position, the cross-sectional area of the longitudinal passageway 338 decreases so that the part of the catheter inserted into the longitudinal passageway 338 is frictionally restrained in the longitudinal passageway 338.

Figure 8:
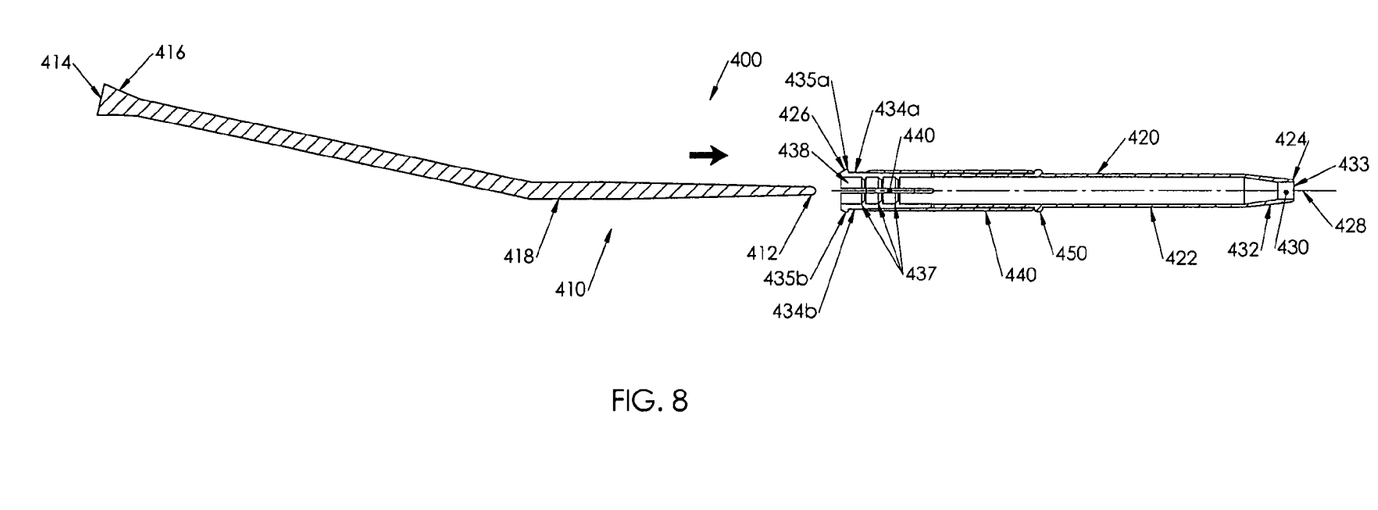
FIG. 8 is a side view, in section of an alternate embodiment of a catheter tunneler adapter, according to the present invention, with a trocar being inserted therein.

A fourth embodiment of the present invention is shown in FIG. 8. In this embodiment, there is a catheter tunneler adapter assembly 400 having a trocar 410, an adapter 420 and a slider 440 slidably disposed about the adapter 420. The trocar 410 has a distal tip 412 a proximal end 414 and a longitudinal shaft 418 disposed between the distal tip 412 and the proximal end 414. Although the distal tip 412 is shown to be pointed, those skilled in the art will recognize that the distal tip 412 may be blunt. The proximal end 414 of the trocar 410 is thicker than the longitudinal shaft 418. The thickness of the trocar 110 increases at the beveled portion 416, located between the proximal end 414 and the longitudinal shaft 418.

The adapter 420 is comprised of a generally tubular body 422, having a distal end 424, a proximal end 426 and a longitudinal axis 428 extending therethrough between the distal end 424 and the proximal end 426. There is, disposed along the longitudinal axis 428 and defined by the generally tubular body 422, a proximal passageway 438, located at the proximal end 426 of the adapter 420 and a distal passageway 430, located at the distal end 424 of the adapter 420. The proximal passageway 438 is in fluid connection with the distal passageway 430. There is, located in the proximal passageway 438, at least one rib 437, extending from the tubular body 422 towards the longitudinal axis 428. While FIG. 8 shows three ribs 437, those skilled in the art will recognize that more or less than three ribs 437 may be used. While the ribs 437 in the current embodiment are pointed, those skilled in the art will recognize that other shapes, such as rounded, may be utilized for the ribs 437.

There is located near the distal tip 424, a tapered portion 432, where the distal passageway 430 decreases in size moving distally along the longitudinal axis 428 to a distal opening 433, located at the distal tip 424. To engage the trocar 410 with the adapter 420, the distal tip 412 of the trocar 410 is inserted into the proximal passageway 438 of the adapter 420 and the trocar 410 is slid distally through the adapter 420. The distal opening 433 is sufficiently large enough to allow the longitudinal shaft 418 of the trocar 410 to pass through as the trocar 410 is slid distally through the adapter 420. The distal opening 433 of the adapter 410 is smaller in diameter than the proximal end 414 of the trocar 410 but larger in diameter than the longitudinal shaft 418 of the trocar 410. The tapered portion 432 of the adapter 420 is sized to frictionally engage the beveled portion 416 of the trocar 410 after the longitudinal shaft 418 of the trocar 410 has been slid through the adapter 420 thereby restricting the proximal end 414 of the trocar 410 from passing through distal opening 433 when the trocar 410 is slid through the adapter 420. The trocar 410 and the distal opening 433 each have a generally circular cross-section, when the cross-sectional view is taken in a plane that is perpendicular to the longitudinal axis 428. There are a plurality of legs (with only legs 434a, 434b being visible in FIG. 8) extending proximally from the tubular body 422 and are disposed about the circumference, that define the proximal passageway 438. Located on the plurality of legs is a plurality of stops (with only stops 435a, 435b being visible) that project outwardly from the longitudinal axis 428. The legs generally are tapered at an angle that is similar to the angle $\beta_2$ shown in FIG. 2.

Referring back to FIG. 8, there are a plurality of bumps 450, located proximally of the legs 434a, 434b disposed about the outside of the tubular body 422 of the adapter 420 and projecting outward away from the longitudinal axis 428. The bumps 450 are sized to restrict movement of the slider 420; however, the bumps 450 are not large enough to completely prohibit movement of the slider 420 thereover. Similar to the disclosures in the other embodiments mentioned herein, the slider 440 is sized to frictionally engage the legs 434a, . . . 434d when slid proximally towards the stops 435a, . . . 435d. Because of the taper of the legs when the slider 440 is slid proximally, the legs are pressed towards the longitudinal axis 428. It is preferable that the slider 440 have a range of motion, between the bumps 450 and the stops that is about two millimeters, however, those skilled in the art will recognize that the slider 440 may have a range of motion greater or less than two millimeters while still performing the same function.

The operation of the fourth embodiment of the assembly 400 is substantially similar to the operation of the other embodiments described herein. However, because the proximal end 414 of the trocar 410 is retained within the distal end 424 of the adapter 420 by the tapered portion 432, the trocar 410 must be inserted into the adapter 420 prior to inserting the catheter lumens 50, 52 into the adapter 420.

Figure 9A:
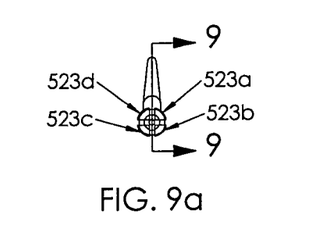
FIG. 9a is a cross-sectional view of the catheter tunneler adapter of FIG. 9.

A fifth embodiment of the present invention is shown in FIGS. 9 and 9a. In this embodiment, there is a catheter tunneler adapter assembly 500 having a trocar 510, an adapter 520 and a slider 540 slidably disposed about the adapter 520. The trocar has a distal tip 512, a proximal end 514 and a longitudinal shaft 513 extending therethrough between the distal tip 512 and the proximal end 514. Although FIG. 9 shows the distal tip 512 to be rounded, those skilled in the art will recognize that the distal tip 512 may be pointed. Although FIG. 9 shows the longitudinal shaft 513 having a bend, those skilled in the art will recognize that the longitudinal shaft 513 may be straight. Located at the proximal end 514 of the trocar 510 is a first rib 515 and a second rib 517. The first rib 515 and the second rib 517 are separated from each other by a circumferential groove 516. The circumferential groove 516 does not have uniform depth and is partially flattened to restrict the trocar 510 from spinning in the adapter 520 after assembly. Although FIG. 9a shows a catheter tunneler adapter assembly 500 having a round cross-section, those skilled in the art will recognize that the assembly 500 may have a cross-section having a shape other than round.

The adapter 520 is comprised of a generally tubular body 522 having a distal end 524, a proximal end 526 and a longitudinal axis 528 extending therethrough between the distal end 524 and the proximal end 526. The generally tubular body 522 of the adapter 520 is tapered so that the proximal end 526 is larger than the distal end 524. A plurality of legs 523a, 523b, 523c and 523d extending proximally about the longitudinal axis 528 are located at the proximal end 526 of the adapter 520. A proximal passageway 530 is disposed about the longitudinal axis 528, and is defined by the tubular body 522 located at the proximal end 526 of the adapter 520. Located at the proximal end 526 of the adapter 520, and extending towards the longitudinal axis 528 is a plurality of barbs 527.

A distal passageway 532 is located at the distal end 524 of the adapter 520. The distal passageway 532 is defined by the generally tubular body 522. Located inside of the distal passageway 532 are a first recess 533 and a second recess 535. Located between the first recess 533 and the second recess 535 is a distal tab 534. Preferably, the first recess 533 is sized to lockingly accommodate the first rib 515 of the trocar 510 and the second recess 535 is sized to lockingly accommodate the second rib 517 of the trocar 510, while the distal tab 534 is sized to fit into the circumferential groove 516 of the trocar 510. The distal tab 534 is partially flattened across its circumference to correspond to the flattened areas in the circumferential groove 516 of the trocar 510.

The slider 540 has a distal end 542, a proximal end 544 and a generally tubular body 546 extending therethrough between the distal end 542 and the proximal end 544. A longitudinal passageway 548 is disposed between the distal end 542 and the proximal end 544 and defined by the generally tubular body 546. Preferably the longitudinal passageway 548 has a proximal passageway 550, extending distally from the proximal end 544 and a distal passageway 552, extending proximally from the distal end 542. Preferably, where the distal passageway 552 and the proximal passageway 550 meet, there is a transition slope 554, wherein the cross-sectional area of the longitudinal passageway 548 decreases while moving distally between the proximal passageway 550 and the distal passageway 552. The distal passageway 552 further decreases in cross-sectional area approaching the distal end 542. Preferably the distal passageway 552 is sized to frictionally engage the distal end 524 of the adapter 520 and has a cross-sectional area that is smaller than the cross-sectional area of the proximal end 526 of the adapter 520. Preferably, the proximal passageway 550 has a cross-sectional area that is slightly larger than the cross-sectional area of the proximal end 526 of the adapter 520.

In use, the fifth embodiment of the catheter tunneler adapter assembly 500 is preferably used with a coaxial catheter, such as the Free Flow™ catheter, manufactured by Medical Components, Inc, of Harleysville, Pa. Preferably, during manufacturing, the proximal end 514 of the trocar 510 is lockingly inserted into the distal passageway 532 of the adapter 520. During insertion, the flattened portion of the circumferential groove 516 is aligned with the corresponding flat portion of the distal tab 534. The slider 540 may be disposed about the adapter 520 during manufacture, or the assembly 500 may be sold in pieces and the slider 540 may be disposed about the adapter 520 during post-sale assembly, prior to use. In use, a coaxial catheter 60 is inserted into the proximal passageway 530 of the adapter 520. The coaxial catheter 60 has a tip lumen 62 and an outer lumen 64. Those skilled in the art will recognize that the assembly may be used to grip a coaxial catheter 60 having a stylet (not shown) as well as a coaxial catheter 60 having no stylet. The slider 540 is then slid distally about the adapter 520 so that the transition slope 554 engages the outer surface of the adapter 520, thereby compressing the plurality of legs 523a, 523b, 523c and 523d towards each other and the longitudinal axis 528 and retaining the catheter 60 in the proximal passageway 530.

Proximal passageway 550 of the slider defines an extended sheath section extending to proximal end 544, that will ensheathe a length of the catheter extending from the adapter's proximal end. Preferably, the coaxial catheter 60 is inserted far enough into the proximal passageway 530 of the adapter 520 that the plurality of legs 523 a, 523b, 523c and 523d, when compressed by the slider 520, grip the outer lumen 64. Those skilled in the art will recognize that the adapter 520 may also be constructed to grip the tip lumen 62. When the slider 540 is slid distally about the adapter 520, the distal passageway 552 of the slider 540 frictionally engages the outer surface of the adapter 520. Although this embodiment of the catheter tunneler adapter assembly 500 is described as being operated to tunnel a coaxial catheter 60, those skilled in the art will recognize that the adapter assembly 500 may be used to tunnel any other type of catheter configuration as well.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. An adapter for connecting a catheter assembly to a trocar comprising:
   a generally tubular body having:
   a first end adapted to engage a connecting end of a trocar; and
   an open second end adapted receive thereinto an end of an at least one catheter lumen and to releasably engage outer surface portions thereof; and
   a longitudinal axis extending between the first end and the second end; and
   a movable locking member movable along the longitudinal axis for urging the second end into engagement with the end of the at least one catheter lumen after insertion into the open second end and thereby releasably connecting the adapter to the at least one catheter lumen, the movable locking member having a minimal transverse dimension and substantially smooth continuous outer surface therealong,
   wherein the open second end includes lumen-engaging inner surface portions adapted to frictionally engage adjacent outer surface portions of the at least one catheter lumen upon being urged thereagainst by the movable locking member and thereby releasably connecting the adapter to the at least one catheter lumen in a frictional fit therewith sufficient to enable pulling thereof through a subcutaneous tunnel defined by the trocar.

2. The adapter according to claim 1, wherein the body further comprises a passageway extending along the longitudinal axis between the first end and the second end.

3. The adapter according to claim 1, wherein the first end comprises a female connection.

4. The adapter according to claim 3, wherein the female connection is threaded.

5. The adapter according to claim 1, wherein the first end is generally tapered.

6. The adapter according to claim 1, wherein the second end is generally tapered.

7. The adapter according to claim 1, wherein the tubular body is generally tapered.

8. The adapter according to claim 1, wherein the second end comprises a plurality of legs extending generally parallel to the longitudinal axis, and wherein the movable locking member comprises a slider slidably disposed about the plurality of legs and slidable between a first position wherein the plurality of legs are in a generally unbiased condition and a second position wherein each of the plurality of legs is biased toward the longitudinal axis.

9. The adapter according to claim 8, wherein the slider is retained on the adapter by at least one tab protruding from the surface of the adapter away from the longitudinal axis.

10. The adapter according to claim 9, wherein the at least one tab comprises two tabs.

11. The adapter according to claim 9, wherein the at least one tab is configured to allow the slider to be slid over the at least one tab toward the second end of the body.

12. The adapter according to claim 9, wherein the at least one tab is configured to restrict the slider from sliding over the at least one tab toward the first end of the body.

13. The adapter according to claim 9, wherein the at least one tab is barbed to restrict the slider from sliding over the at least one tab toward the first end of the body.

14. The adapter according to claim 9, wherein the at least one tab comprises at least one rounded nub.

15. The adapter according to claim 1, wherein the adapter is constructed from a polymer.

16. The adapter according to claim 1, wherein the at least one catheter lumen end comprises at least two catheter lumens having side-by-side end portions.

17. The adapter according to claim 1, wherein the second end comprises a generally oval cross-section.

18. The adapter according to claim 1, wherein the second end comprises a generally circular cross-section.

19. The adapter according to claim 1, wherein the second end comprises a plurality of legs extending generally parallel to the longitudinal axis, wherein the legs are joined by a plurality of flexible grooves.

20. The adapter according to claim 19, wherein the movable locking member comprises a slider slidably disposed about the plurality of legs and slidable between a first position wherein the plurality of legs are in a generally unbiased condition and a second position wherein each of the plurality of legs is biased toward the longitudinal axis.

21. The adapter according to claim 1, wherein the catheter assembly comprises a dual lumen catheter having two side-by-side catheter lumen ends.

22. The adapter according to claim 1, wherein the catheter assembly comprises a coaxial catheter.

23. An adapter for connecting a catheter of a vascular catheter assembly implantable into the vasculature of a patient, to a trocar for subcutaneous tunneling of the catheter, comprising:
a generally tubular body having:
a first end adapted to engage a connecting end of a trocar; and
an open second end adapted receive thereinto an end of an at least one catheter lumen of an implantable vascular catheter and to releasably engage outer surface portions thereof; and
a longitudinal axis extending between the first end and the second end;
and
a movable locking member for urging the second end into engagement with the end of the at least one catheter lumen after insertion into the open second end and thereby releasably connecting the adapter to the at least one catheter lumen,
wherein the second end comprises a plurality of legs extending generally parallel to the longitudinal axis, and wherein the movable locking member comprises a slider slidably disposed about the plurality of legs and slidable between a first position wherein the plurality of legs are in a generally unbiased condition and a second position wherein each of the plurality of legs is biased toward the longitudinal axis, and
wherein the plurality of legs includes lumen-engaging inner surface portions adapted to frictionally engage adjacent outer surface portions of the at least one flexible compressible catheter lumen upon being urged thereagainst by the slider when the slider is disposed in the second position and thereby releasably connecting the adapter to the at least one catheter lumen in a frictional fit therewith sufficient to enable pulling thereof through a subcutaneous tunnel defined by the trocar.

24. The adapter according to claim 23, wherein, when the slider is disposed from the first position toward the second position, the slider is moved from the first end of the body toward the second end of the body.

25. The adapter according to claim 23, wherein, when the slider is disposed from the second position toward the first position, the slider is moved from the second end of the body toward the first end of the body.

26. An adapter assembly for connecting a catheter assembly to a trocar for subcutaneous tunneling of the catheter assembly, the adapter assembly comprising:
a generally tubular body having:
a distal end comprising a tapered tip;
a proximal end comprising a plurality of legs associated with an end portion of at least one catheter lumen;
a longitudinal axis extending therethrough between the distal end and the proximal end;
and
a slider is slidably disposed about the tubular body;
wherein, the slider is slidable between a first position and a second position;
wherein, when the slider is in the first position, the plurality of legs is generally unbiased and disposed about outer surface portions of the at least one catheter lumen;
wherein, when the slider is in the second position, the plurality of legs are generally biased towards the longitudinal axis and into frictional engagement with the adjacent outer surface portions of the at least one catheter lumen inserted therebetween with sufficient frictional engagement to enable pulling of the at least one catheter lumen through a subcutaneous tunnel;
wherein the tubular body is releasably connectable to a trocar, and
wherein the slider has a minimal transverse dimension and substantially smooth continuous outer surface thereaIong.

27. The adapter assembly of claim 26, wherein the slider comprises an elongated proximal portion.

28. A catheter tunneling assembly for subcutaneously tunneling at least one implantable vascular catheter, comprising:
a distal portion including:
a distal tip;
a proximal end; and
an elongated body extending between the distal tip and the proximal end;
and
a proximal portion including:
a generally elongated body having a distal end and an open proximal end and a longitudinal axis extending therethrough between the distal end and the proximal end, the open proximal end being sized and shaped to surround an end of an at least one catheter inserted thereinto, wherein the proximal end of the distal portion is connected to the distal end of the proximal portion, wherein the open proximal end of the proximal portion comprises a locking member movable along the longitudinal axis for urging the open proximal end into engagement with the end of the at least one catheter after its axial insertion into the open proximal end and thereby releasably connecting to the at least one catheter, and wherein the axially movable locking member has a minimal transverse dimension and substantially smooth continuous outer surface therealong.

29. The catheter tunneling assembly according to claim 28, wherein the movable locking member is a slider disposed about the proximal portion.

30. The catheter tunneling assembly of claim 28, wherein the open proximal end includes catheter-engaging inner surface portions adapted to frictionally and releasably engage adjacent outer surface portions of the at least one catheter upon being urged thereagainst by the movable locking member and thereby releasably connecting the proximal portion to the at least one catheter in a frictional fit therewith sufficient to enable pulling thereof through a subcutaneous tunnel defined by the distal portion.

* * * * *